United States Patent
Kuroda et al.

(10) Patent No.: US 8,372,386 B2
(45) Date of Patent: Feb. 12, 2013

(54) KERATOTIC PLUG REMOVING COMPOSITION

(75) Inventors: Shigeru Kuroda, Tokyo (JP); Toshiya Morikawa, Tokyo (JP)

(73) Assignee: Kao Corporation, Tokyo (JP)

( * ) Notice: Subject to any disclaimer, the term of this patent is extended or adjusted under 35 U.S.C. 154(b) by 931 days.

(21) Appl. No.: 11/994,655

(22) PCT Filed: Jul. 5, 2006

(86) PCT No.: PCT/JP2006/313423
§ 371 (c)(1),
(2), (4) Date: Aug. 4, 2008

(87) PCT Pub. No.: WO2007/007618
PCT Pub. Date: Jan. 18, 2007

(65) Prior Publication Data
US 2009/0123410 A1    May 14, 2009

(30) Foreign Application Priority Data
Jul. 8, 2005 (JP) ................................. 2005-199703

(51) Int. Cl.
*A61K 31/74* (2006.01)
*A01N 25/34* (2006.01)

(52) U.S. Cl. ............... 424/78.11; 424/78.03; 424/78.05; 424/402

(58) Field of Classification Search ............... 424/78.11, 424/70.122, 78.03, 78.05, 402, 79.11
See application file for complete search history.

(56) References Cited

U.S. PATENT DOCUMENTS

| | | | | |
|---|---|---|---|---|
| 5,470,563 A | * | 11/1995 | Tanaka et al. | 424/448 |
| 5,512,277 A | * | 4/1996 | Uemura et al. | 424/78.03 |
| 6,312,714 B1 | * | 11/2001 | Prosise et al. | 424/443 |
| 6,419,935 B1 | * | 7/2002 | Gueret | 424/401 |
| 7,597,780 B2 | * | 10/2009 | Buder et al. | 162/164.4 |
| 2006/0039885 A1 | * | 2/2006 | Nishio | 424/70.122 |

FOREIGN PATENT DOCUMENTS

| | | |
|---|---|---|
| JP | 63-46163 | 2/1988 |
| JP | 4 234307 | 8/1992 |
| JP | 5 97627 | 4/1993 |
| JP | 5 221843 | 8/1993 |
| JP | 8 59451 | 3/1996 |
| JP | 10-16109 | 1/1998 |
| JP | 10-101527 | 4/1998 |
| JP | 11 12127 | 1/1999 |
| JP | 2000-225185 | 8/2000 |
| JP | 2001 89571 | 4/2001 |
| WO | 97 32567 | 9/1997 |
| WO | WO 2004/039347 A1 * | 5/2004 |

OTHER PUBLICATIONS

"Polysilicone-16", International Cosmetic Ingredient Dictionary and Handbook Tenth Edition, vol. 2, p. 1457, 2004.
Office Action issued Sep. 9, 2011 in Chinese patent Application No. 200680024772.2 (with English translation).
Office Action issued Jun. 1, 2011, in Chinese Patent Application No. 200680024772.2 with English translation.

\* cited by examiner

*Primary Examiner* — Gina C Justice
(74) *Attorney, Agent, or Firm* — Oblon, Spivak, McClelland, Maier & Neustadt, L.L.P.

(57) ABSTRACT

The present invention relates to a keratotic plug remover composition including a polymer compound having a salt-forming group, and (a) an amino-modified silicone and/or (b) a polyoxyalkylene/dimethyl polysiloxane block copolymer, and a sheet for removing keratotic plugs including a non-woven fabric substrate impregnated with the above composition. The keratotic plug remover composition and the sheet for removing keratotic plugs according to the present invention are enhanced in keratotic plug removing effect without increasing a pain of users when peeling the sheet pack from the skin.

18 Claims, No Drawings

KERATOTIC PLUG REMOVING COMPOSITION

CROSS REFERENCES TO RELATED APPLICATIONS

This application is a 371 of International Patent Application No. PCT/JP2006/313423, filed on Jul. 5, 2006, and claims priority to Japanese Patent Application No. 2005-199703, filed on Jul. 8, 2005.

TECHNICAL FIELD

The present invention relates to keratotic plug remover compositions applicable to pack cosmetics for removing keratotic plugs, aged keratin and smears of sebum, and peel-off type sheets for removing keratotic plugs using the compositions.

BACKGROUND ART

As peel-off type pack cosmetics for removing keratotic plugs, aged keratin and smears of sebum, there have been proposed the sheet-like packs obtained by applying a film-forming pack composition onto a moisture-permeable substrate (for example, JP 11-12127A corresponding to WO 97/32567). The sheet-like packs have advantages such as a less surface stickiness upon use, a shortened drying time, no tearing upon peeling off and a less peel residue.

DISCLOSURE OF THE INVENTION

With the recent tendency that sheet-like packs are extensively and generally used, the sheet-like packs as disclosed in JP 11-12127A have been improved in keratotic plug removing effect by further enhancing adhesion to the skin. However, when the adhesion of the sheet-like packs to the skin is enhanced, the users tend to undergo an increased pain when peeling the packs from the skin. Therefore, it has now been strongly demanded to develop and provide a sheet-like pack that is still more improved in keratotic plug removing effect by further enhancing its adhesion to the skin without causing the users to suffer the increased pain when peeling the pack from the skin.

The present invention aims at providing a keratotic plug remover composition applicable to a peel-off type sheet-like pack for removing keratotic plugs, aged keratin and smears of sebum which is enhanced in keratotic plug removing effect without increasing a pain of users when peeling the pack from the skin, as well as such a sheet for removal of keratotic plugs.

The inventors have found that a keratotic plug remover composition containing a polymer compound having a salt-forming group and a silicone derivative having a specific structure is capable of effectively removing keratotic plugs and smears without damage to the skin. The present invention has been accomplished on the basis of the finding.

Thus, the present invention relates to a keratotic plug remover composition comprising a polymer compound having a salt-forming group, and (a) an amino-modified silicone and/or (b) a polyoxyalkylene/dimethyl polysiloxane block copolymer, and a sheet for removing keratotic plugs comprising a nonwoven fabric substrate impregnated with the above composition.

The keratotic plug remover composition of the present invention is capable of being peeled off from the skin of users after drying without damage to the skin and feeling of a pain, and effectively removing keratotic plugs, so that pores of the skin are prevented from becoming conspicuous, and an inside of pores of the skin can be kept clean.

PREFERRED EMBODIMENTS FOR CARRYING OUT THE INVENTION

The salt-forming group of the polymer compound used in the present invention is not particularly limited as long as it is a group capable of forming a salt in the presence of an acid or a base, and may be either an anionic group, a cationic group and an amphoteric group. Specific examples of the salt-forming group include a carboxyl group, a sulfonic acid residue, a sulfuric acid residue, a phosphoric acid residue, a nitric acid residue, an amino group and an ammonium group. The polymer compound may contain two or more kinds of these groups in one molecule thereof. In view of effective removal of keratotic plugs, among these groups, preferred are anionic groups and cationic groups.

Specific examples of the polymer compound are as follows. Examples of natural or semi-synthetic compounds include mucopolysaccharides such as hyaluronic acid, sodium hyaluronate and sodium chondroitin sulfate; and hemicelluloses such as alginic acid, sodium alginate, ammonium alginate, carboxymethyl cellulose sodium salt and carboxymethyl amylose. As the polymer compound, synthetic compounds are more preferred. Examples of the synthetic compounds include polymers obtained by polymerizing at least one monomer selected from the group consisting of the below-mentioned anionic monomers, cationic monomers and amphoteric monomers, copolymers obtained by copolymerizing these monomers with the other monomers, e.g., vinyl monomers such as (meth)acrylic esters and styrene, and mixtures of these polymers.

Examples of the anionic monomers include unsaturated carboxylic acid monomers such as acrylic acid (AA), methacrylic acid (MA), maleic acid and itaconic acid, and anhydrides and salts of these acids; unsaturated sulfonic acid monomers such as styrenesulfonic acid and 2-acrylamido-2-methylpropanesulfonic acid (AMPS) and salts thereof; and unsaturated phosphoric acid monomers such as vinylphosphonic acid and acid phosphoxyethyl (meth)acrylate.

Examples of the cationic monomers include dialkylamino group-containing (meth)acrylate esters or (meth)acrylamides such as dimethylaminoethyl acrylate (DMAEA), dimethylaminoethyl methacrylate (DMAEMA), dimethylaminopropyl acrylamide (DMAPAAm) and dimethylaminopropyl methacrylamide (DMAPMAAm); dialkylamino group-containing styrenes such as dimethylaminostyrene (DMASt) and dimethylaminomethyl styrene (DMAMSt); vinyl pyridines such as 4-vinyl pyridine and 2-vinyl pyridine; and compounds obtained by quaternarizing these monomers using a known quaternarizing agent such as an alkyl halide, a benzyl halide, an alkyl- or aryl-sulfonic acid and a dialkyl sulfate.

Examples of the amphoteric monomers include N-(3-sulfopropyl)-N-acryloyloxyethyl-N,N-dimethyl ammonium betaine, N-(3-sulfopropyl)-N-methacryloylamidopropyl-N,N-dimethyl ammonium betaine, N-(3-carboxymethyl)-N-methacryloylamidopropyl-N,N-dimethyl ammonium betaine, N-(3-sulfopropyl)-N-methacryloyloxyethyl-N,N-dimethyl ammonium betaine and N-carboxymethyl-N-methacryloyloxyethyl-N,N-dimethyl ammonium betaine.

When the salt-forming group of these polymer compounds is not ionized, the polymer compounds are preferably neutralized with a known acid, e.g., inorganic acids such as hydrochloric acid and sulfuric acid; and organic acids such as acetic acid, propionic acid, lactic acid, succinic acid and glycolic acid, or a known base, e.g., tertiary amines such as trimethylamine and triethylamine; ammonia; and sodium hydroxide.

The polymer compound preferably has a molecular weight of 10,000 to 3,000,000 and more preferably 100,000 to 1,000,000. When the molecular weight of the polymer compound is 10,000 or more, the resultant film can exhibit a sufficient strength and impart an adequate tenseness to the skin and, therefore, is free from tearing upon peeling. On the other hand, when the molecular weight of the polymer compound is 3,000,000 or less, the production of the polymer compound can be carried out advantageously.

The content of the polymer compound in the keratotic plug remover composition of the present invention is preferably from 0.01 to 70% by weight and more preferably from 5 to 40% by weight on the basis of a whole amount of the keratotic plug remover composition.

The polymer compound may be usually used in the form of a solution obtained by dissolving the polymer compound in a solvent. The solvent used for preparing the polymer solution is not particularly limited as long as the polymer compound can be stably dissolved therein and the solvent is safe for the skin. Examples of the solvent include water, ethanol and isopropyl alcohol. The amount of the solvent may be appropriately determined depending upon the polymer compound, optional components and types of the usage, and in general, is preferably in the range of 30 to 99.49% by weight on the basis of a whole amount of the keratotic plug remover composition.

The amino-modified silicone (a) used in the present invention is not particularly limited as long as it contains an amino group in a side chain bonded to a silicon atom. Specific examples of the preferred amino-modified silicone (a) include those compounds represented by the following general formula (1):

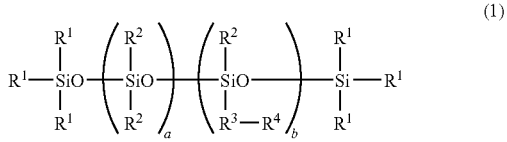

(1)

In the general formula (1), the $R^1$ groups each independently represent a monovalent hydrocarbon group, a hydroxyl group or an alkoxy group. Specific examples of the monovalent hydrocarbon group include an alkyl group and an aryl group. Among these group, preferred are alkyl groups having 1 to 3 carbon atoms, and more preferred is methyl. Specific examples of the alkoxy group include alkoxy groups having 1 to 15 carbon atoms. Among these alkoxy groups, preferred are alkoxy groups having 10 to 15 carbon atoms.

In the general formula (1), the $R^2$ groups each independently represent a monovalent hydrocarbon group. Specific examples of the monovalent hydrocarbon group as $R^2$ include alkyl group having 1 to 6 carbon atoms such as methyl, ethyl, propyl, butyl, pentyl and hexyl; aryl groups having 6 to 10 carbon atoms such as phenyl, tolyl and xylyl; and aralkyl groups having 7 to 10 carbon atoms such as benzyl and phenethyl. Among these groups, preferred are alkyl groups, and methyl group is particularly preferred.

In the general formula (1), the $R^3$ groups each independently represent a divalent hydrocarbon group having 1 to 10 carbon atoms. Specific examples of the divalent hydrocarbon group as $R^3$ include alkylene groups such as methylene, ethylene, trimethylene, propylene, tetramethylene, methyl trimethylene, ethyl ethylene and dimethyl ethylene; and alkylene-arylene groups such as the group represented by the formula: $-(CH_2)_2-C_6H_4-$. Among these groups, preferred are alkylene groups having 2 to 4 carbon atoms.

In the general formula (1), the $R^4$ groups each independently represent a group represented by the following formula (2) or (3):

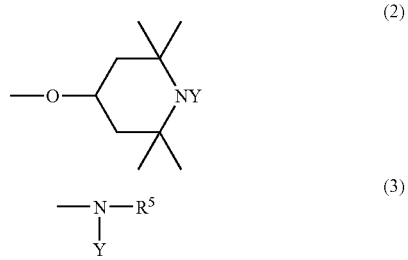

Among these groups, preferred is the group represented by the formula (3).

In the formula (2) or (3), the Y groups each independently represent a hydrogen atom or a group represented by the formula: $-CH_2-CH(OH)-R^3-OH$ wherein $R^3$ is the same as defined above. The group represented by the formula: $-CH_2-CH(OH)-R^3-OH$ is preferably 2,3-dihydroxypropyl.

In the formula (3), $R^5$ is a hydrogen atom or a group represented by the formula: $-R^3NY_2$ wherein Y and $R^3$ are the same as defined above. Examples of the preferred groups represented by the formula: $-R^3NY_2$ include N-(2,3-dihydroxypropyl)aminoethyl and N,N-bis(2,3-dihydroxypropyl)aminoethyl.

Meanwhile, in the formula (2) or (3), all of the Y groups are not hydrogen atoms at the same time.

In the general formula (1), a is a number of 25 to 1,000 and preferably 75 to 400, and b is a number of 1 to 200 and preferably 1 to 20.

In addition, the amino-modified silicone used in the present invention may also include synthetic compounds obtained by reacting an amino-modified silicone with an epoxy functional compound such as glycidol, for example, bis($C_{13}$ to $C_{15}$ alkoxy)propylene glycol amodimethicone (INCI name: BIS (C13-C15 ALKOXY)PG AMODIMETHICONE), such as "8600 Hydrophillic Softner (tradename)" available from Dow Corning Co. Further, as the amino-modified silicone, there may also be used compounds represented by the following formula (4):

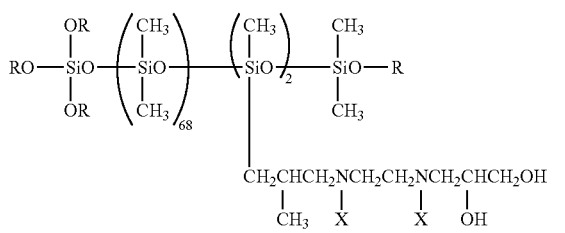

wherein R is $C_{13}H_{27}$ to $C_{15}H_{31}$; and X is a group composed of 75% of $-CH_2CH(OH)CH_2OH$ and 25% of a hydrogen atom.

Examples of commercially available products of the amino-modified silicone represented by the formula (4) include "8500 Conditioning Agent" (CAS No. 237753-63-8)

available from Dow Corning Co., and "JP-8500 Conditioning Agent" available from Toray Dow Corning Co., Ltd.

Specific examples of the other suitable commercially available products of the amino-modified silicone include amino-modified silicone oils such as "SF8451C" (viscosity: 600 mm$^2$/s; amino equivalent: 1700 g/mol) available from Toray Dow Corning Co., Ltd., "SF8452C" (viscosity: 700 mm$^2$/s; amino equivalent: 6400 g/mol) available from Toray Dow Corning Co., Ltd., "SF8457C" (viscosity: 1200 mm$^2$/s; amino equivalent: 1800 g/mol) available from Toray Dow Corning Co., Ltd., "KF8003" (viscosity: 1850 mm$^2$/s; amino equivalent: 2000 g/mol) available from GE Toshiba Silicone Co., Ltd., and "KF867" (viscosity: 1300 mm$^2$/s; amino equivalent: 1700 g/mol) available from GE Toshiba Silicone Co., Ltd.; and amodimethicone emulsions such as "SM8704C" (amino equivalent: 1800 g/mol) available from Toray Dow Corning Co., Ltd. The amino-modified silicone oils may also be used in the form of an emulsion. The amino-modified silicone emulsion may be prepared by mechanical emulsification method in which the amino-modified silicone is mechanically mixed with water under a high shear condition, chemical emulsification method in which the amino-modified silicone is emulsified using water or an emulsifier or combination of these emulsification methods, or by emulsion polymerization.

Next, the polyoxyalkylene/dimethyl polysiloxane block copolymer (b) used in the present invention contains a polyoxyalkylene group in a dimethyl polysiloxane main chain thereof, and represented by the following general formula (5). The polyoxyalkylene/dimethyl polysiloxane block copolymer (b) is different from the conventional so-called polyether-modified silicones containing a polyoxyalkylene group bonded to a siloxane side chain thereof (hereinafter occasionally referred to merely as "polyether-modified silicone").

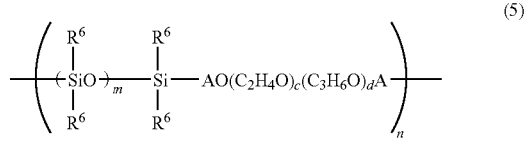

(5)

In the general formula (5), $R^6$ is an aliphatic saturated monovalent hydrocarbon group and preferably methyl; A is a saturated alkylene group having 2 to 8 carbon atoms and preferably a group represented by the formula: —CH$_2$CH$_2$CH$_2$—; m is a number of 1 to 300 on the average and preferably 10 to 100 on the average; n is a number of 2 to 20 on the average and preferably 5 to 15 on the average; and c and d are respectively a number of 0 to 50 on the average, c is preferably a number of 2 to 30 on the average and d is preferably a number of 0 to 10 on the average with the proviso that a sum of c and d is 2 or more (c+d≧2).

Specific examples of commercially available products of the polyoxyalkylene/dimethyl polysiloxane block copolymer (b) include "FZ-2203", "FZ-2222", "FZ-2231", "FZ-2404" and "FZ-2405" all available from Toray Dow Corning Co., Ltd.

Further, in addition to the commercially available chemical materials, the polyoxyalkylene/dimethyl polysiloxane block copolymer (b) may also be produced by conventionally known methods, for example, by the polycondensation reaction using polyoxyalkylene and both terminal-reactive diorganopolysiloxane.

The amino-modified silicones (a) and the polyoxyalkylene/dimethyl polysiloxane block copolymers (b) may be respectively used in combination of any two or more thereof. Also, the amino-modified silicone (a) may be used in combination of the polyoxyalkylene/dimethyl polysiloxane block copolymer (b). The content of the amino-modified silicone (a) and/or the polyoxyalkylene/dimethyl polysiloxane block copolymer (b) is preferably from 0.5 to 25% by weight, more preferably from 1 to 20% by weight and still more preferably from 1.5 to 15% by weight on the basis of the amount of the composition of the present invention in view of good keratotic plug removing effect and less pain upon peeling.

The keratotic plug remover composition of the present invention may also contain other components used for ordinary cosmetics unless the addition thereof adversely affects the aimed effects of the present invention. Examples of the other components include ethylene glycol, diethylene glycol, triethylene glycol and polyethylene glycols having a larger number of carbon atoms; propylene glycol, dipropylene glycol and polypropylene glycols having a larger number of carbon atoms; butylene glycols such as 1,3-butylene glycol and 1,4-butylene glycol; glycerol, diglycerol and polyglycerols having a larger number of carbon atoms; sugar alcohols such as sorbitol, mannitol, xylitol and multitol; ethyleneoxide (hereinafter referred to merely as "EO") adducts and propyleneoxide (hereinafter referred to merely as "PO") adducts of glycerols, EO adducts and PO adducts of sugar alcohols, monosaccharides such as galactose, glucose and fructose as well as EO adducts and PO adducts thereof, disaccharides such as maltose and lactose as well as EO adducts and PO adducts thereof, chemical agents such as vitamins, anti-inflammatory agents, bactericides, activators and ultraviolet absorbers; inorganic thickening agents such as montmorillonite, saponite, hectorite and silicic anhydride; polysaccharides such as carageenan, xanthan gum, sodium alginate, pullulan, methyl cellulose, hydroxyethyl cellulose and hydroxypropyl cellulose; other polymers, e.g., synthetic polymers such as polyvinyl pyrrolidone; extender pigments such as titanium oxide, kaolin, mica, sericite, zinc white, talc, silica, barium sulfate and alumina; pigments, e.g., polymer powders such as polymethyl methacrylate powder and nylon powder.

The keratotic plug remover composition of the present invention may be used as a pack agent by directly applying the composition onto the skin, or may be used in the form of a sheet by applying the composition to a substrate such as woven or nonwoven fabrics of cotton cloth, staple fiber, tetron and nylons, and plastic sheets. The substrate is preferably made of a nonwoven fabric in view of low costs, high yield and good feeling though not limited thereto. The fineness of fibers forming the nonwoven fabric is preferably about several μm to 50 μm in diameter, and more preferably 30 μm or less in diameter in view of good permeation through property of cosmetic in the sheet pack and good feeling.

Also, the substrate is preferably in the form of a multi-layer moisture-permeable substrate composed of a water-repellent layer and a hydrophilic layer. In this case, the cosmetic containing the keratotic plug remover composition is included in and supported by the hydrophilic layer.

The keratotic plug remover of the present invention may be produced according to the method for production of ordinary pack agents or sheet-like packs. The keratotic plugs can be removed using the keratotic plug remover of the present invention by the same methods as used for ordinary pack agents or sheet-like packs. Namely, for example, the pack agent containing the keratotic plug remover of the present invention may be applied to the skin, and peeled off from the skin after drying.

EXAMPLES

Examples 1 to 5 and Comparative Examples 1 to 3

A water-repellent nonwoven fabric made of polypropylene fiber (15 g/m$^2$) and a hydrophilic nonwoven fabric made of a mixture of polypropylene fiber and rayon fiber (mixing ratio is 4:6) (10 g/m$^2$) were laminated together by a heat emboss method to produce a water-permeable substrate having a two-layer structure.

Next, the respective components shown in Table 1 were uniformly mixed with each other at ambient temperature using a stirring machine, and deaerated under reduced pressure, thereby preparing a keratotic plug remover composition.

The thus obtained keratotic plug remover composition was cast over a release sheet made of a polypropylene film to form a paste layer having a uniform thickness. Immediately after the cast-coating, the above-obtained water-permeable substrate was laminated on the paste layer such that the hydrophilic surface faced the paste layer, and passed through a hot air dryer at 80° C. to evaporate water therefrom. Upon the drying, the thickness of the paste layer was finally adjusted to 100 to 130 µm, thereby obtaining a sheet-like pack for removing keratotic plugs.

The thus obtained sheet-like pack for removing keratotic plugs was cut into halves, and one half adhered onto a washed facial surface of a subject on one side of the nose under such a condition that an adequate amount of water still remained thereon. The number of people as the subject whose right side face was attached with a test pack to be evaluated and left side face was attached with a control pack was adjusted to be identical to the number of people whose right side face was contrarily attached with the control pack and left side face was attached with the test pack to be evaluated. After drying, the sheet-like pack for removing keratotic plugs was peeled off from the face of each subject to evaluate a "keratotic plug removing rate" and an "extent of pain upon peeling" thereof according to the following ratings.

(1) Keratotic Plug Removing Rate

The number of the keratotic plugs removed on the sheet-like pack was counted, and evaluated by a relative value obtained assuming that the number of keratotic plugs removed in Comparative Example 1 using the control pack was 100.

(2) Extent of Pain upon Peeling

The extent of pain upon peeling was evaluated by a sensory evaluation test according to the following three ranks.

○: Feeling a less pain than that of Comparative Example 1

Δ: Feeling a pain substantially identical to that of Comparative Example 1

X: Feeling a more pain than that of Comparative Example 1

TABLE 1

|  | Examples | | | | | Comparative Examples | | |
| --- | --- | --- | --- | --- | --- | --- | --- | --- |
|  | 1 | 2 | 3 | 4 | 5 | 1 | 2 | 3 |
| Components (weight %) | | | | | | | | |
| Polymethacryloyloxy-ethyl trimethyl ammonium chloride (INCI name: POLYQUATERNIUM-37; molecular weight: 400,000) | 25 | 25 | 25 | 25 | 25 | 25 | — | — |
| Polyvinyl pyrrolidone | — | — | — | — | — | — | 20 | — |
| Polyvinyl alcohol | — | — | — | — | — | — | — | 20 |
| Silicic anhydride | 20 | 20 | 20 | 20 | 20 | 20 | 20 | 20 |
| Glycerol | 6 | 6 | 6 | 6 | 6 | 6 | 6 | 6 |
| Polyoxyethylene-modified dimethyl polysiloxane*[1] | 0.5 | 0.5 | 0.5 | 0.5 | 0.5 | 0.5 | 0.5 | 0.5 |
| Bis($C_{13}$-$C_{15}$ alkoxy) propylene glycol amodimethicone*[2] | 1 | 3 | — | — | — | — | — | — |
| Polyoxyalkylene/ dimethyl polysiloxane block Copolymer (HLB = 1)*[3] | — | — | 1 | 3 | 5 | — | — | — |
| Purified water | Balance | Balance | Balance | Balance | Balance | Balance | Balance | Balance |
| Evaluation results | | | | | | | | |
| Keratotic plug removing rate (%) | 142 | 163 | 150 | 146 | 125 | 100 | 5 | 5 |
| Extent of pain upon peeling | ○ | ○ | ○ | ○ | ○ | ○ | ○ | ○ |

Note:
*[1]Polyether-modified silicone (INCI name: PEG-12 DIMETHICONE; "SH-3771E" (tradename) available from Toray Dow Corning Co., Ltd.)
*[2]Amino-modified silicone (INCI name: BIS($C_{13}$-$C_{15}$ ALKOXY)PG AMODIMETHICONE; "JP-8500 Conditioning Agent" (tradename) available from Toray Dow Corning Co., Ltd.)
*[3]Polyoxyalkylene/dimethyl polysiloxane block copolymer (INCI name: POLYSILICONE-13; "FZ-2203" (tradename) available from Toray Dow Corning Co., Ltd.)

INDUSTRIAL APPLICABILITY

The keratotic plug remover composition and the sheet for removing keratotic plugs according to the present invention can be applied to a peel-off type sheet-like pack for removing keratotic plugs, aged keratin and smears of sebum, and can exhibit an enhanced keratotic plug removing effect without increasing a pain upon peeling the pack from the skin.

The invention claimed is:

1. A keratotic plug remover composition, comprising:
polymethacrylolyoxy-ethyl trimethyl ammonium chloride; and
at least one compound represented by formula (5):

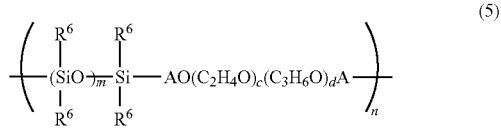

wherein:
R6 is an aliphatic saturated monovalent hydrocarbon group;
A is a saturated alkylene group having 2 to 8 carbon atoms;
m is a number of 1 to 300 on the average;
n is a number of 2 to 20 on the average; and
c and d are respectively a number of 0 to 50 on the average, with the proviso that a sum of c and d is 2 or more (c +d≧2),
wherein said at least one compound represented by formula (5) is present in an amount of from 1 to 5% by weight based on the total weight of said composition, and said polymethacryloyloxy-ethyl trimethyl ammonium chloride is present in an amount of from 5 to 40% by weight based on the total weight of said composition.

2. A sheet for removing keratotic plugs, comprising a nonwoven fabric substrate impregnated with at least one composition as defined in claim 1.

3. A method for removing keratotic plugs, which comprises:
(i) plastering skin with a keratotic plug remover composition according to claim 1;
(ii) drying said composition, to obtain a dried composition; and
(iii) peeling said dried composition from said skin.

4. A method for removing keratotic plugs, which comprises:
(i) plastering skin with a sheet according to claim 2;
(ii) drying said sheet, to obtain a dried sheet; and
(iii) peeling said dried sheet from said skin.

5. A keratotic plug remover composition according to claim 1, wherein
R6 is methyl.

6. A keratotic plug remover composition according to claim 1, wherein A is $-CH_2CH_2CH_2-$.

7. A keratotic plug remover composition according to claim 1, wherein:
R6 is methyl;
A is $-CH_2CH_2CH_2-$;
m is a number of 10 to 100 on the average;
n is a number of 5 to 15 on the average;
c is a number of 2 to 30 on the average; and
d is a number of 0 to 10 on the average.

8. A sheet for removing keratotic plugs, comprising a nonwoven fabric substrate impregnated with at least one composition according to claim 7.

9. A method for removing keratotic plugs, which comprises:
(i) plastering skin with a keratotic plug remover composition according to claim 7;
(ii) drying said composition, to obtain a dried composition; and
(iii) peeling said dried composition from said skin.

10. A method for removing keratotic plugs, which comprises:
(i) plastering skin with a sheet according to claim 8;
(ii) drying said sheet, to obtain a dried sheet; and
(iii) peeling said dried sheet from said skin.

11. A keratotic plug remover composition, comprising:
polymethacrylolyoxy-ethyl trimethyl ammonium chloride; and
bis-(C13-C15-alkoxy)propylene glycol amodimethicone,
wherein said bis-(C13-C15-alkoxy)propylene glycol amodimethicone is present in an amount of from 1 to 5% by weight based on the total weight of said composition, and said polymethacryloyloxy-ethyl trimethyl ammonium chloride is present in an amount of from 5 to 40% by weight based on the total weight of said composition.

12. A sheet for removing keratotic plugs, comprising a nonwoven fabric substrate impregnated with at least one composition as defined in claim 11.

13. A method for removing keratotic plugs, which comprises:
(i) plastering skin with a keratotic plug remover composition according to claim 11;
(ii) drying said composition, to obtain a dried composition; and
(iii) peeling said dried composition from said skin.

14. A method for removing keratotic plugs, which comprises:
(i) plastering skin with a sheet according to claim 12;
(ii) drying said sheet, to obtain a dried sheet; and
(iii) peeling said dried sheet from said skin.

15. A keratotic plug remover composition, according to claim 11,
wherein said bis-(C13-C15-alkoxy)propylene glycol amodimethicone is present in an amount of from 1 to 3% by weight based on the total weight of said composition.

16. A sheet for removing keratotic plugs, comprising a nonwoven fabric substrate impregnated with at least one composition as defined in claim 15.

17. A method for removing keratotic plugs, which comprises:
(i) plastering skin with a keratotic plug remover composition according to claim 15;
(ii) drying said composition, to obtain a dried composition; and
(iii) peeling said dried composition from said skin.

18. A method for removing keratotic plugs, which comprises:
(i) plastering skin with a sheet according to claim 16;
(ii) drying said sheet, to obtain a dried sheet; and
(iii) peeling said dried sheet from said skin.

* * * * *